United States Patent
Chang et al.

(10) Patent No.: US 8,148,066 B2
(45) Date of Patent: Apr. 3, 2012

(54) METHOD OF NUCLEIC ACID HYBRIDIZATION

(76) Inventors: Chung-Cheng Chang, Keelung (TW); Jau-Der Chen, Keelung (TW); Pei-Tai Chen, Keelung (TW)

( * ) Notice: Subject to any disclaimer, the term of this patent is extended or adjusted under 35 U.S.C. 154(b) by 1211 days.

(21) Appl. No.: 11/778,251

(22) Filed: Jul. 16, 2007

(65) Prior Publication Data
US 2008/0194804 A1 Aug. 14, 2008

(30) Foreign Application Priority Data
Feb. 14, 2007 (TW) .............................. 96105504 A (51) Int. Cl.
*C12Q 1/68* (2006.01)
*C12P 19/34* (2006.01)
*C12M 1/34* (2006.01)
*C07H 21/02* (2006.01)
*C07H 21/04* (2006.01)

(52) U.S. Cl. .... 435/6.1; 435/6.11; 435/91.1; 435/287.2; 536/23.1; 536/24.3

(58) Field of Classification Search ............ 435/6, 91.1, 435/183, 283.1, 287.1, 287.2, 6.1, 6.11; 536/23.1, 536/24.3, 24.33; 422/50, 68.1
See application file for complete search history.

(56) References Cited

U.S. PATENT DOCUMENTS
5,932,413 A * 8/1999 Celebuski .................... 435/6.11
2005/0112139 A1* 5/2005 Karp .......................... 424/188.1

OTHER PUBLICATIONS
Levy et al., Removal of contaminant nucleic acids by nitrocellulose filtration during pharmaceutical-grade plasmid DNA processing. Journal of Biotechnology, 78, 197-205, 2000.*

* cited by examiner

*Primary Examiner* — Frank W Lu
(74) *Attorney, Agent, or Firm* — Rabin & Berdo, P.C.

(57) ABSTRACT

The present invention relates to a nucleic acid hybridization method and in particular to a method using a microfluidic chip-based hybridization device with modified procedures which shows the advantages of simplicity and efficiency. The method of the present invention is to mix the test nucleic acid and the probe nucleic acid in advance, feed the solution into a hybridization device with a porous substrate, let the nucleic acid to be analyzed absorb into the substrate. The washing solution is then injected into the same device to wash out the unhybridized probes and the signals of hybridization absorbed on the substrate are detected for analysis. The conventional 2-step approach for the hybridization of the nucleic acid to be analyzed and the probe is combined into one step by the method of the invention provided here, which simplifies the necessary steps and shorten the time needed for hybridization reaction and detection.

10 Claims, 5 Drawing Sheets

METHOD OF NUCLEIC ACID HYBRIDIZATION

BACKGROUND OF THE INVENTION

1. Field of the Invention

The present invention relates to a hybridization method for nucleic acids, and in particular to a method using a hybridization device with the procedures modified, which shows advantages of simplicity and efficiency.

2. The Prior Arts

Nucleic acid hybridization with a probe is a method popularly used to identify the target DNA from a sample containing the desired gene or the nucleic acid fragment. Conventionally, the hybridization reaction was carried out by blotting or transferring the sample DNA to a substrate such as a membrane, hybridizing and pairing the nucleic acid with a probe having specificity, and then presenting the result of the hybridization by the probe-labeled present molecule in a presenting method such as coloring method, chemiluminescence method, and radiography method and so on. A blotting method in which a DNA sample transferred to the membrane by electrophoresis gel is hybridized with the probe is referred to as Southern blotting method. A blotting method in which a RNA sample transferred is hybridized is referred to as Northern blotting method. Other blotting method in which the nucleic acid to be analyzed is directly dropped is referred to as dot-/slot-/spot blotting method according to the dropping area. The dot-/slot-/spot blotting method is usually applied among the abovementioned methods in general qualitative analysis or in large batches of analysis, because the analyzing time can be shortened due to the needlessness of electrophoresis for separation and transfer, and the cost is low due to the needlessness of electrophoresis and transferring devises and various related agents.

The conventional blotting method is to directly drop the nucleic acid to be analyzed on the surface of a membrane. The nucleic acid to be analyzed is fixed by heating or radiation with ultraviolet to form covalent crosslinkage with the membrane thereon to prevent it from falling off in the subsequent hybridization and washing processes. Under the conventional condition, the nucleic acid to be analyzed is dropped in a wet membrane, which will further be diffused, penetrated and absorbed in the membrane surface. Therefore, it takes long time for the nucleic acid to be analyzed to absorb. On the other hand, during the addition of the nucleic acid probe contained in the blocking reagent for hybridization, the probe can only be diffused on the membrane surface in a similar way as the nucleic acid to be analyzed, finds and base-pairs with the complementary nucleic acid to be analyzed through Brownian motion. Therefore, the conventional hybridization reaction needs many procedures and more than 10 hours of the reaction time to proceed. The reaction cannot be finished in a short time even when the result is urgent needed. In addition, the method is non-economical if a lot of time and agents are used for simple qualitative tests of nucleic acid. Accordingly, it is necessary to develop a rapid blotting method or device in which the time and procedures for blotting analysis can be simplified and the background noise can be lowered. This will greatly enhances the efficiency, shortens the time needed for the experiment, and reduces the cost of the materials for either the simple tests or the large batches of analysis.

SUMMARY OF THE INVENTION

In order to overcome the drawbacks of the conventional methods during hybridization reaction, including absorption of nucleic acid being analyzed and probes addition for base pairing, as well as to increase the sensitivity for more nucleic acid to be analyzed to absorb rapidly into the surface of the substrate, the present invention herein provides a nucleic acid hybridization method using a hybridization device, in which the test nucleic acid is mixed with the nucleic acid probe for base pairing in advance. The mixed solution is fed into a hybridization device, followed by washing with washing solution. The signals of hybridization absorbed on the substrate are then detected for analysis. This method according to the present invention thus simplifies the necessary procedures and shortens the time needed.

To fulfill the objectives of the present invention, a method of nucleic acid hybridization is provided, which comprises the steps of:

(1) providing a test nucleic acid and a nucleic acid probe;
(2) mixing the test nucleic acid and the probe for base pairing;
(3) providing a hybridization device, wherein a hybridization region is installed with a porous substrate, the hybridization region is connected to at least one first inlet/outlet hole and at least one second inlet/outlet hole respectively;
(4) feeding the mixed solution obtained from step (2) into at least one of the inlet/outlet holes to run through the inside of substrate, and flowing out from at least one of the rest inlet/outlet holes, to let the test nucleic acid absorb to the substrate;
(5) providing a washing solution, feeding into at least one of the inlet/outlet holes to run through the inside of substrate, and washing out from at least one of the rest inlet/outlet holes to remove the nucleic acid probe unhybridized to the test nucleic acid from step (2); and
(6) detecting the hybridization signals on the substrate having been subjected to step (5).

The hybridization device in the invention includes, but is not limited to, a microfluidic chip. The hybridization device can be composed of an upper basal plate and a lower basal plate. Both the plates are stacked up to form a hybridization region, in which a porous substrate is installed inside. The upper basal plate links to at least one first inlet/outlet hole in the hybridization region. To the lateral side of the hybridization region, there is at least one second inlet/outlet hole linked. The shapes and the thickness of the hybridization region are not particularly defined, which are easily adjusted with the structure of the substrates. An interstice with a defined width is reserved for the lateral side of the substrate and hybridization region to let the reaction solution enter into the substrate. On the other hand, the substrate can be in a dry state before the reaction to drive the solution rapidly travels the substrate through capillary action. The diameter of the pores in the substrate is around, but not limited to, 0.01-50 μm to let the nucleic acid probe penetrate easily. The materials for the substrate include, but are not limited to, nylon membranes and nitrocellulose membrane.

The mixing procedure of the test nucleic acid and the probe in step (2) saves the time for the first addition of the test nucleic acid, and the addition of the nucleic acid probe respectively, and the hybridization steps are also being simplified. In addition, the hybridization region in the hybridization device can be a chamber or an open space. The mixed solution has to run through the substrate in the closed space due to the limitation of the space and the pressure of the fluid. Therefore the large nucleic acid molecules to be analyzed (or the probe base-paired nucleic acid to be analyzed) can be blocked out along the side of substrate with a small cavity. At the same time, the probes without base-pairing can be washed out from the cavity with the washing solution under the fluid pressure. Consequently, with the alternative washing method, the background noise can be lowered and the sensitivity can be increased.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

BRIEF DESCRIPTION OF THE DRAWINGS

The related drawings in connection with the detailed description of the present invention to be made later are described briefly as follows, in which.

DETAILED DESCRIPTION OF THE PREFERRED EMBODIMENT

Figure 1:
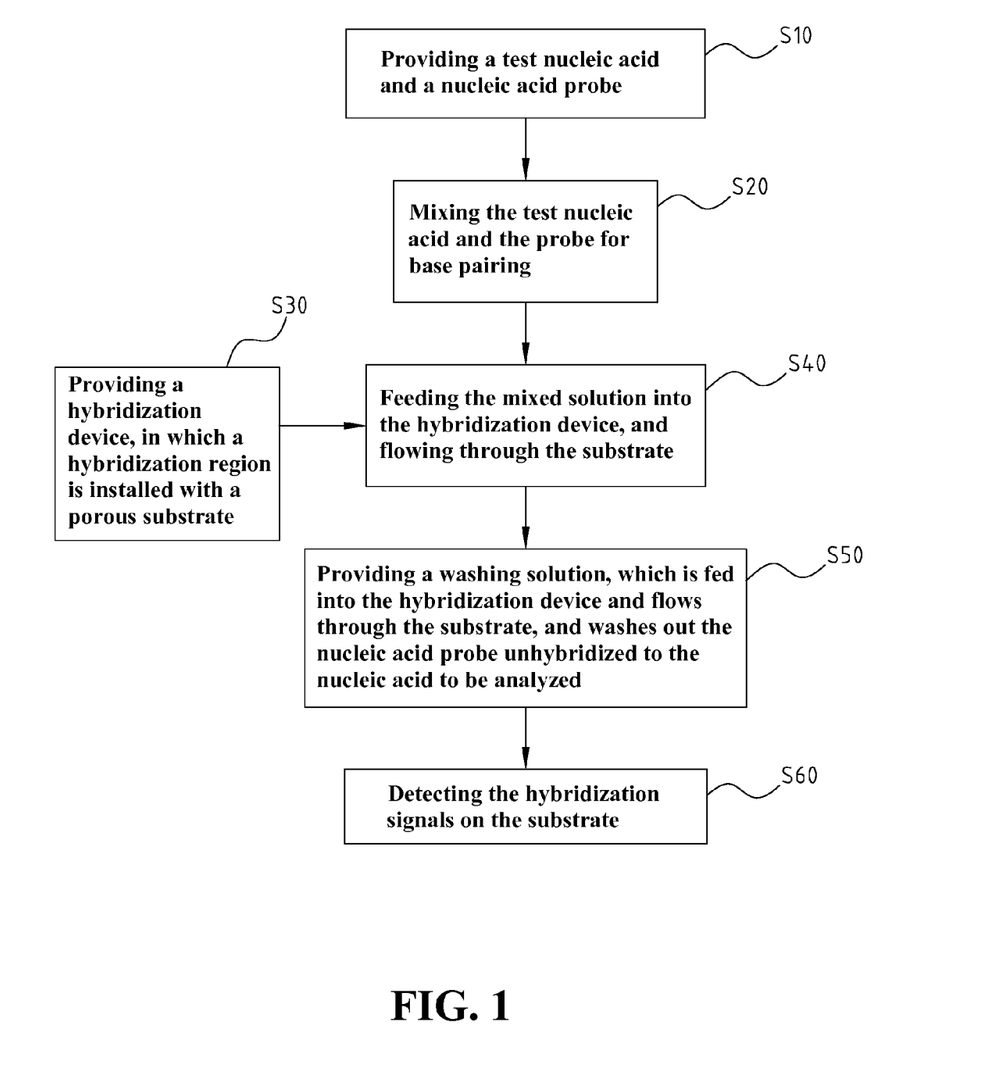
FIG. 1 is a flow chart showing the embodiment of the present invention.

Referring to FIG. 1, a flow chart shows the embodiment of the present invention. The nucleic acid hybridization method of the invention is an alternative to the conventional methods which the nucleic acid to be analyzed is firstly transferred and fixed to the substrate, and is base-paired with the nucleic acid probe. The method of the present invention is to mix for base pairing the target nucleic acid and the probe nucleic acid in advance, feed the solution into a substrate and let the nucleic acid to be analyzed (or the probe base-paired nucleic acid to be analyzed) absorb into the substrate, wash out the un-bound probes and detect the signals of hybridization absorbed on the substrate.

The nucleic acid hybridization method of the invention comprises: step S10, providing a test nucleic acid and a nucleic acid probe; step S20, mixing the test nucleic acid and the probe for base pairing; step S30, providing a hybridization device, in which a hybridization region is installed with a porous substrate; step S40, feeding the mixed solution obtained from step S20 into the hybridization device to run through the substrate to let the test nucleic acid absorb to the substrate; step S50, providing a washing solution, feeding into the hybridization device, washing out the nucleic acid probe which has not been bound to the test nucleic acid; followed by step S60, detecting the hybridization signals on the substrate to yield the results.

Suitable detection methods may be used according to the labeling markers of the probe. There are many commercial kits for chemiluminescent, fluorescent and calorimetric methods of detection, which also include agents and solution for preparing the probe. Among the calorimetric methods of detection, DIG Luminescent Detection Kit using the digoxigenin (DIG) is widely used at present, in which an anti-DIG antibody bonded with alkaline dephosphorylase is reacted with a coloring substrate such as nitroblue tetrazolium (NBT), 5-bromo-4-chloro-3-indolyl phosphate (BCIP) or CSPD® for color detection. Base on the description herein, it will be understood by those skilled in the art that the nucleic acid probe may be labeled with biotin during the preparation thereof, and subsequently detected with streptavidin and enzyme. In addition, radioactive detection methods using the radioactive isotopes $^{32}P$ or $^{35}S$, or fluorescence-based detection methods using hexachlorofluorescein (HEX), Cy3 and Cy5 may also be used to label the probes. Other detection methods include, but are not limited to, photoelectric detection methods such as impedance detection, capacitance detection, resistance detection, and electrochemical detection; mass detection or weight detection methods.

Figure 2A:
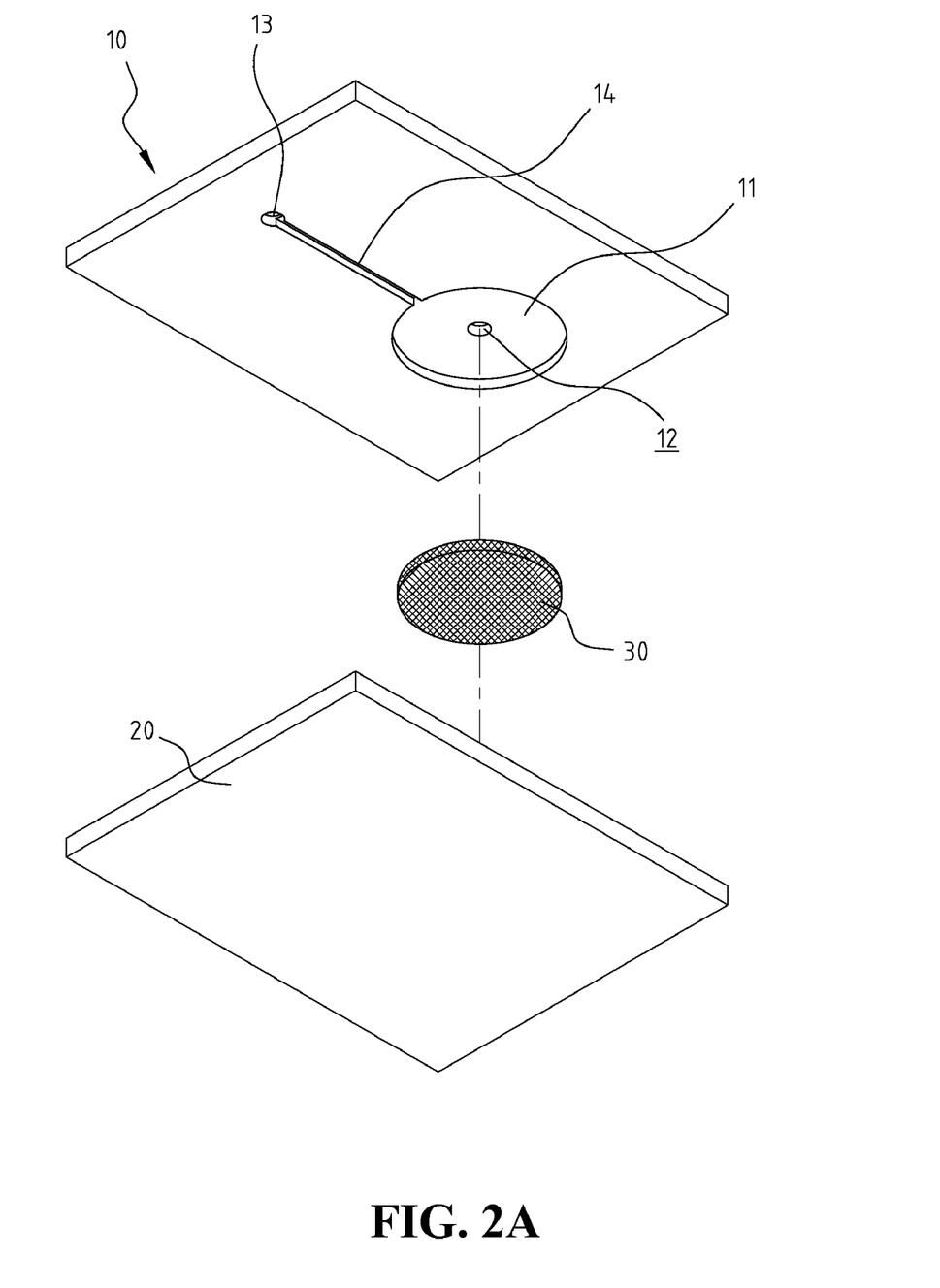
FIG. 2A illustrates the three-dimensional schematic representation of the hybridization device in the embodiment of the present invention.

Referring to FIG. 2A, the three-dimensional schematic representation of the hybridization device in the first embodiment of the present invention is shown. The hybridization device of the invention comprises an upper basal plate 10, a lower basal plate 20 and a substrate 30, wherein the upper basal plate 10 and the lower basal plate 20 are stacked together. And the substrate 30 is installed in the hybridization region 11 of the upper basal plate 10.

Figure 2B:
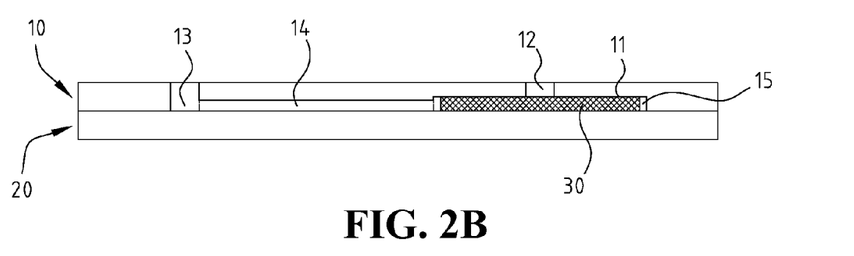
FIG. 2B shows the cross section diagram of the hybridization device in the embodiment of the present invention.
Figure 2C:
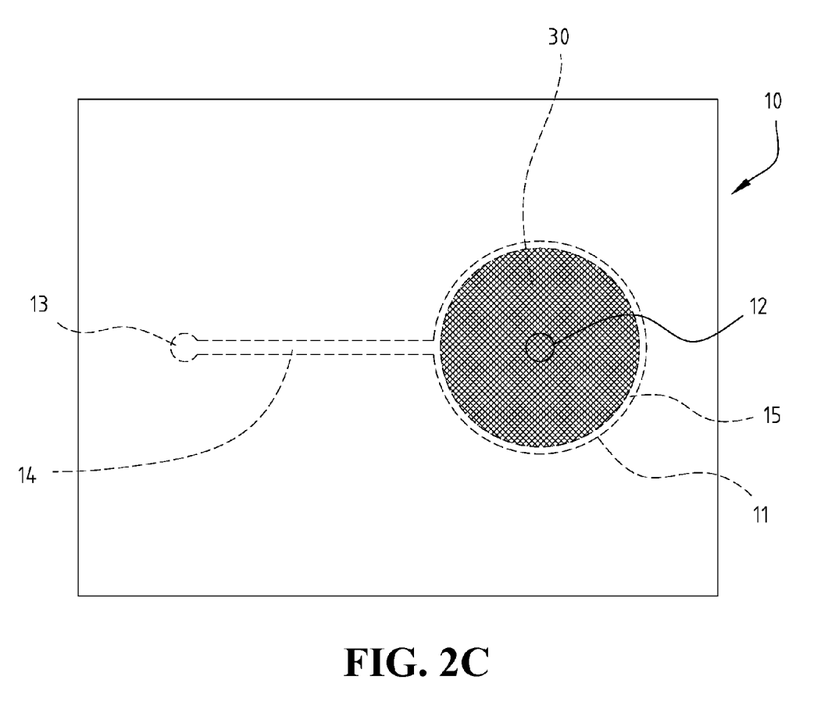
FIG. 2C shows the top view diagram of the hybridization device in the embodiment of the present invention.

Referring to FIGS. 2A, 2B and 2C, the hybridization region set up in the upper basal plate 10 is like a disk chamber. However, there is no limitation for the shape, the size and the thickness of the hybridization region 11, which can also be a tetrahedral chamber. There is a first inlet/outlet hole 12 run through the middle of the hybridization region 11. The opening position of the first inlet/outlet hole 12 is not limited, which can be adjusted according to the position of the other inlet/outlet hole so that the flow pathway of the reaction solution can be spread all over the inside of substrate 30. Therefore, the number of the first inlet/outlet hole 12 is also not limited. The first inlet/outlet hole 12 can be further connected to a microfluidic channel or other inlet/outlet holes (not shown in the Figure) to facilitate the feeding of solution or the allocation of each microfluidic channel.

The first microfluidic channel 14 is connected to the side of the hybridization region 11 and further linked to the second inlet/outlet hole 13. The number and the position of the first microfluidic channel 14 and the second inlet/outlet hole 13 are not limited, which can also be adjusted according to the flow pathways. In addition, the top and bottom surfaces of the substrate 30 and the hybridization region 11 can be touched so that the substrate 30 is gripped in the hybridization region 11, whereas a predetermined interstice of 0.05 to 0.2 mm, preferably 0.1 mm, is provided between the lateral side of the substrate 30 and the hybridization region 11.

Still referring to FIGS. 2A and 2B, the hybridization region 11, the first microfluidic channel 14 and the second inlet/outlet hole 13 are finally formed between the upper basal plate 10 and the lower basal plate 20 of the hybridization device. Therefore, the hybridization region 11, the first microfluidic channel 14 and the second inlet/outlet hole 13 are not only limited to be located on the upper basal plate 10, but also on the lower basal plate 20. In addition, they may also form corresponding chamber, microfluidic channel or inlet/outlet hole on the upper basal plate 10 or the lower basal plate 20 respectively after both of them are bond. Besides separately manufactured, the upper basal plate 10 and the lower basal plate 20 can also be manufactured integrally to form the abovementioned hybridization region 11, first microfluidic channel 14 and second inlet/outlet hole 13. The hybridization region 11 in the hybridization device is not limited to be a chamber or an open space; the structure disposition is depend on the purpose of test.

The hybridization device of the first embodiment includes, but is not limited to, a microfluidic chip, a smaller sized chip including nanofluidic chip, or any other structure which is suitable to the present invention. Quartz, glass, or the like can be used as the substrate of the microfluidic chip, and the capillary microchannels are formed by wet etching, where a layer of quartz or glass is covered on the top of the capillary microchannels to produce chips equipped with closed microchannels or chambers. Alternatively, the hybridization device can be made of hard polymers, such as polymethyl methacrylate (PMMA), or polycarbonate (PC). Firstly, the master mold is made with substrates like quartz using subsequent wet-etching. Microchannels are embossed onto PMMA or PC plates by hot embossing process, followed by covering lower basal plate with the same material. The hybridization device of the present invention can also be made of soft polymers, such as polydimethyl siloxane (PDMS). Because of its good fluidity, the hot embossing process is not needed. Therefore the master mold will not be damaged easily, and can be manufactured in a large scale. This makes PDMS a preferable substrate, though not limited thereto.

Substrate 30 is made of porous materials, or fillers with porous materials, which includes, but not limited to, a nylon membrane or a nitrocellulose membrane. The nylon membrane can be positive charged or neutral, and the pore size can be 0.01 to 50 μm for nylon membranes or nitrocellulose membranes. The proper size depends on the molecular weight of the test nucleic acid. Large size of nucleic acid molecule needs the larger pores, preferably from 0.2 μm to 0.45 μm. Moreover, the substrate can be in a dry state so that the injected target nucleic acid can be adsorbed rapidly.

Figure 2D:
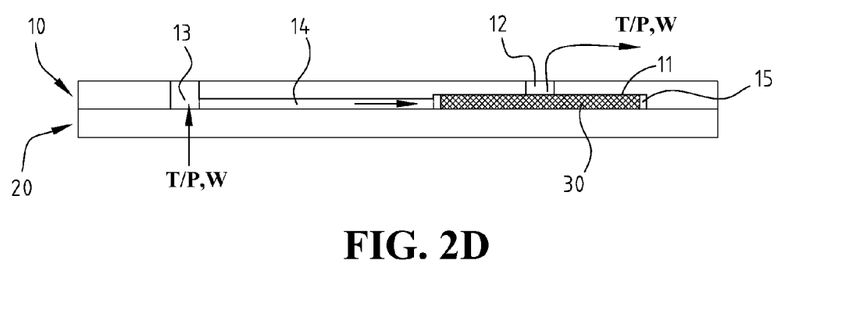
FIG. 2D shows the directions of fluid flow during hybridization in the embodiment of the present invention.

Referring to FIG. 2D, the diagram represents direction of the fluid flow in hybridization device in the first embodiment of the present invention. Firstly, the test nucleic acid and the probe are mixed for base pairing. The mixed solution T/P is fed into the second inlet/outlet hole 13, pass through first microfluidic channel 14 to enter hybridization region 11. After filling the interstice 15 around the periphery space of the substrate 30, the mixed solution T/P diffuses across the substrate 30 from the side to the center of substrate 30, and discharged to the outside via the first inlet/outlet hole 12. The test nucleic acid is blocked and absorbed around the side surface of substrate 30 due to the size of molecule during diffusion. The probe base-paired to the nucleic acid to be analyzed is also blocked and absorbed in the periphery of the substrate 30. The nucleic acid probe is labeled with chromogenic molecules in order to show the results of hybridization reaction. The nucleic acid probe can be labeled with a radioisotope, a fluorescent compound, or an enzyme, though not limited thereto.

After the process of base pairing, the unhybridized nucleic acid probes are washed away. The washing solution W is fed via the second inlet/outlet hole 13 during the washing process. The washing solution W is flushed into the hybridization region 11 through the first microfluidic channel 14. When the washing solution W is flushed into the hybridization region 11, it fills the interstice 15 firstly, then diffuses from the side of the substrate 30 toward the center, and finally is discharged out via the first inlet/outlet hole 12. The nucleic acid probe, which is a small molecule relatively, can be easily and rapidly flushed out from the pores of the substrate 30 at the same time. Therefore, this method shortens the time needed for washing and reduces the background noise. Lastly, the results of hybridization reaction are obtained through the detection of the nucleic acid probes labeled with chromogenic molecules. If the nucleic acid probes are not labeled with chromogenic molecules, the results of hybridization reaction can also be obtained through impedance detection method, capacitance detection method, resistance detection method, electrochemical detection method, or molecular weight measuring method, though not limited thereto.

The inlet/outlet hole for feeding the hybridization mixed solution T/P or the washing solution W is not limited to the inlet/outlet hole 13. The mixed solution T/P could be fed into the first inlet/outlet hole 12 to enter hybridization region 11 and run through from the center to the side of substrate 30. After filling the interstice 15 around the periphery space of the substrate 30, the mixed solution pass through first microfluidic channel 14 to discharge to the outside via the second inlet/outlet hole 13. The test nucleic acid is blocked and absorbed around the surface of substrate 30 due to the size of molecule during diffusion.

According to the generally known polymerase chain reaction (PCR), the annealing of the primer and the test nucleic acid only takes less than one minute. Accordingly, in the present invention, the test nucleic acid and the nucleic acid probe can be base paired in rather a short time after mixing. And the unhybridized probes can be washed out rapidly by washing solution after feeding into the hybridization device. Therefore, the processes from the base pairing of the test nucleic acid and the nucleic acid probe to the washing step can be finished in a very short time. The steps for hybridization can be simplified and the timing for hybridization and detection is shortened with the method according to the present invention.

EXAMPLE 1

DNA Hybridization Using the Hybridization Device

Firstly, the hybridization device is prepared according to the diagram of FIG. 2A. The hybridization device is formed with a PDMS upper basal plate 10 stacked to a glass lower basal plate 20. Both the plates are stacked up to form a disk chamber like hybridization region 11, and a round nylon membrane (substrate 30) with a diameter of 6 mm, pore size of 0.2 μm is installed in the hybridization region 11. The width of interstice 15 between the peripheral side of the membrane and the lateral side of hybridization region 11 is 0.1 mm. The first inlet/outlet hole 12 and the second inlet/outlet hole 13 are linked to connection tubes and pumps to facilitate the transportation of solution as the structure of common microfluidic chips.

The test nucleic acid and the nucleic acid probe solution were prepared for hybridization. 5 μl (100 ng) of extracted DNA from *E. tarda* DNA (experiment group), and *A. hydrophila* DNA (control group) were respectively aliquoted and heated to 94° C. for 3 min to denature the double strand DNA into single strand DNA. The DNA was maintained at 50° C. in a heating block. The nucleic acid probe, which can be complementary to the *E. tarda* DNA but not the *A. hydrophila* DNA, was prepared and labeled with hexachlorofluorescein (HEX) fluorescent dye. 5 μl (100 pmole) of the probe was respectively added into the above-denatured single strand DNA. The solution to proceed mixing and base-pairing. The power of the heating block was turned off and cooled to room temperature.

The energy levels of HEX fluorescent dye in this embodiment are changed by excitation of laser beam. The changes of the emitted fluorescence intensity can be converted to the voltages. Therefore the hybridization between the test nucleic acid and the nucleic acid probe can be detected by the measurement in milli volts. The voltage value of nylon membrane alone was detected and recorded as "background" value. The result is shown in FIG. 3.

The hybridization mixed solution T/P was fed into the second inlet/outlet hole 13 with a flow rate of 200-300 µl/min and an operation pressure of 35 kPa. The hybridization mixed solution T/P passed through first microfluidic channel 14 and entered hybridization region 11 after injection. After filling the interstice 15 around the periphery space of the substrate 30, the mixed solution T/P diffused across the substrate 30 from the side to the center of substrate 30, and discharged to the outside via the first inlet/outlet hole 12. The voltage change of the "unwashed" group is shown in FIG. 3. The test nucleic acid was blocked and absorbed around the side surface of substrate 30 due to the size of molecule during diffusion. The probe base-paired to the test nucleic acid was also blocked and absorbed in the periphery of the substrate 30. At the same time, the unhybridized nucleic acid probe would fill in the pores of the substrate 30.

The unhybridized nucleic acid probe was then washed out with 2.5 ml washing solution W (0.1×SSC containing 0.1% (w/v) SDS) at a flow rate of 300 µl/min and an operation pressure of 35 kPa for the hybridization device. The washing solution W was fed into the same second inlet/outlet hole 13, passed through first microfluidic channel 14 and entered hybridization region 11 after injection. After filling the interstice 15 around the periphery space of the substrate 30, the washing solution W diffused across the substrate 30 from the side to the center of substrate 30, and discharged to the outside via the first inlet/outlet hole 12. Another 2.5 ml of the washing solution W was fed again as the second washing step. The voltage changes of the "washed once" group and the "washed twice" group are measured and shown in FIG. 3.

Figure 3:
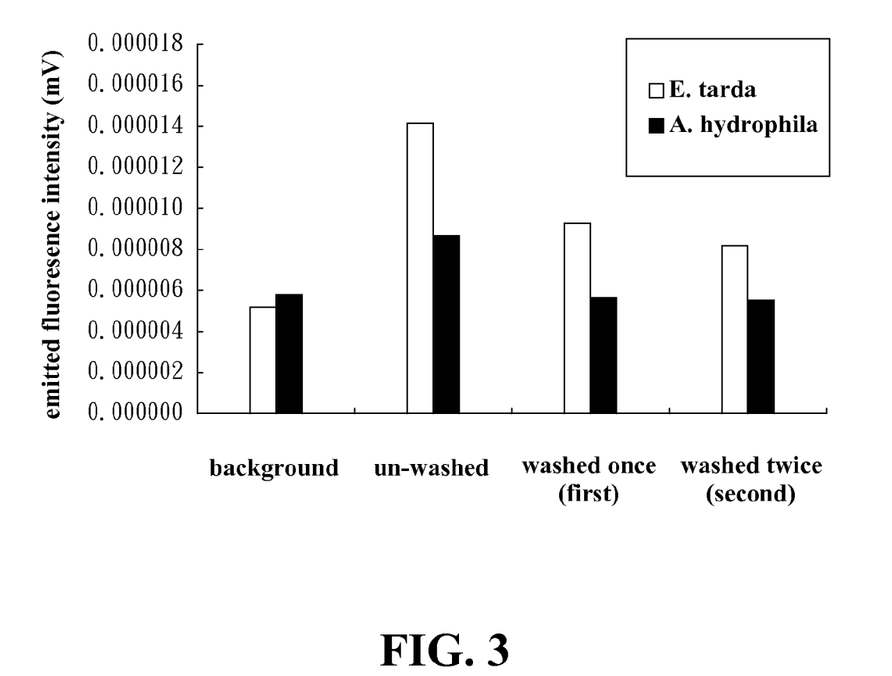
FIG. 3 illustrates the results after DNA hybridization in the embodiment of the present invention. The groups include, from left to right on the horizontal X-axis, control, un-washed, washed once (first) and washed twice (second), and the vertical Y-axis shows the emitted fluorescence intensity (mV)

FIG. 3 illustrates the results of this embodiment after DNA hybridization using the hybridization device of the invention. The vertical Y-axis shows the emitted fluorescence intensity (mV). The groups in the horizontal X-axis are "background" control, "un-washed", "washed once (first)" and "washed twice (second)" respectively. The emitted fluorescence intensity mV was obtained after the fluorescence was converted to the voltage value. The original positive and negative values of voltages were adjusted to positive values for comparison purpose.

The nucleic acid probe was blocked and absorbed along the periphery space of substrate after base-paired with the DNA of *E. tarda* when the hybridization mixed solution are fed into the hybridization device. The non-base-paired nucleic acid probe (labeled with fluorescent dye) was also filled in the pores of the substrate. Therefore the voltage value measured could be as high as 0.00001415 mV before washing. The values dropped to 0.00000929 after the first washing process, and 0.00000819 mV after the second washing process respectively since the non-base-paired nucleic acid probe was flushed out, which are still higher than the background value of 0.00000515 mV. Hence the results are positive for the hybridization. The method of the invention can therefore identify the hybridization between test DNA and the nucleic acid probe, and further confirms the existence of the desired target sequence in the test nucleic acid.

On the other hand, the DNA sequence of *A. hydrophilia* could not base-pair with the nucleic acid probe. The voltage value measured is also higher before washing because the nucleic acid probe (labeled with fluorescent dye) was also filled in the pores of the substrate. The values dropped to 0.0000055 mV after the first and the second washing processes respectively, which is quite close to the background value of 0.00000579 mV. The feasibility of the method of the invention is further confirmed with no occurrence of pseudo-positive result.

EXAMPLE 2

RNA Hybridization Using the Hybridization Device

The test RNA and the nucleic acid probe solution were prepared for hybridization. 5 µl (500 ng) of extracted RNA from *E. tarda* RNA (experiment group), and *A. hydrophilia* RNA (control group) were respectively aliquoted and heated to 94° C. for 3 min to denature. The RNA was maintained at 70° C. in a heating block. The nucleic acid probe, which can be complementary to the *E. tarda* RNA but not the *A. hydrophilia* RNA, was prepared and labeled with hexachlorofluorescein (HEX) fluorescent dye. 5 µl (100 pmole) of the probe was respectively added into the above-denatured RNA. They were mixed at 70° C. and base-paired for 10 min. The heating block was removed and the samples were cooled to room temperature.

The hybridization mixed solution T/P mentioned above was fed into the second inlet/outlet hole 13 with a flow rate of 200-300 µl/min and an operation pressure of 35 kPa. The hybridization mixed solution T/P passed through first microfluidic channel 14 and entered hybridization region 11 after injection. After filling the interstice 15 around the periphery space of the substrate 30, the mixed solution T/P diffused across the substrate 30 from the side to the center of substrate 30, and discharged to the outside via the first inlet/outlet hole 12. The voltage change was detected (the result of the "unwashed" group is shown in FIG. 4, while refers to the background value for the voltage value of nylon membrane alone).

The unhybridized nucleic acid probe was then washed out with 2.5 ml washing solution W (0.1×SSC containing 0.1% (w/v) SDS) at a flow rate of 300 µl/min and an operation pressure of 35 kPa for the hybridization device. The washing solution W was fed into the same second inlet/outlet hole 13, passed through first microfluidic channel 14 and entered hybridization region 11 after injection. After filling the interstice 15 around the periphery space of the substrate 30, the washing solution W diffused across the substrate 30 from the side to the center of substrate 30, and discharged to the outside via the first inlet/outlet hole 12. Another 2.5 ml of the washing solution W was fed again as the second washing step. The voltage changes of the "washed once" group and the "washed twice" group are measured and shown in FIG. 4.

Figure 4:
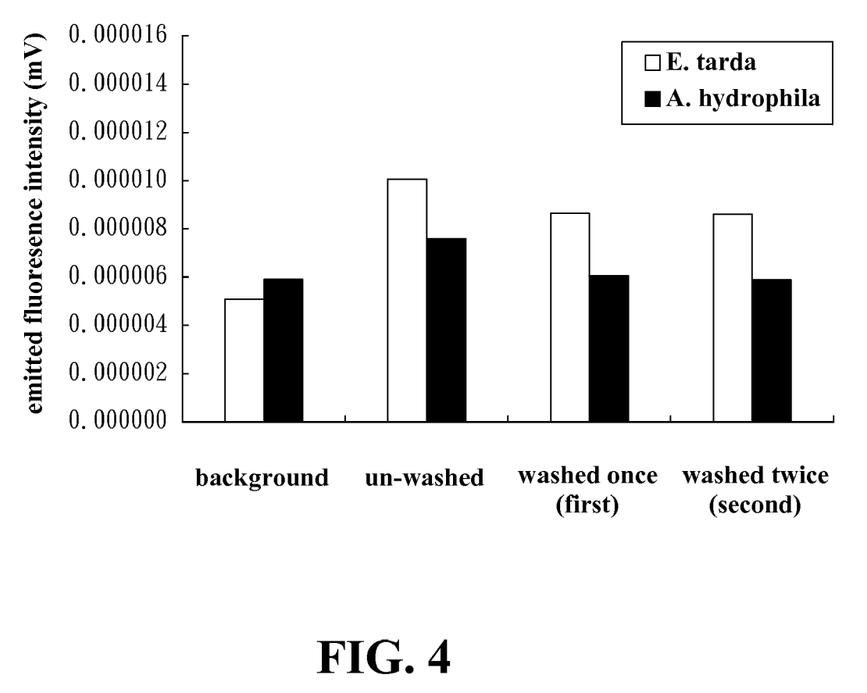
FIG. 4 illustrates the results after RNA hybridization in the embodiment of the present invention. The groups include, from left to right on the X-axis, as control, un-washed, washed once (first) and washed twice (second), and the Y-axis shows the emitted fluorescence intensity (mV).

FIG. 4 illustrates the results of this embodiment after RNA hybridization using the hybridization device of the invention. The vertical Y-axis shows the emitted fluorescence intensity (mV). The groups in the horizontal X-axis are "background" control, "un-washed", "washed once (first)" and "washed twice (second)" respectively. The emitted fluorescence intensity mV was obtained after the fluorescence was converted to the voltage value. The original positive and negative values of voltages were adjusted to positive values for comparison purpose.

The nucleic acid probe was blocked and absorbed along the periphery space of substrate after base-paired with the RNA of *E. tarda* when the hybridization mixed solution are fed into the hybridization device. The non-base-paired nucleic acid probe (labeled with fluorescent dye) was also filled in the pores of the substrate. Therefore the voltage value measured could be as high as 0.00001005 mV before washing. The values dropped to 0.00000865 after the first washing process, and 0.00000861 mV after the second washing process respectively since the non-base-paired nucleic acid probe was flushed out, which are still higher than the background value of 0.00000508 mV. Hence the results are positive for the hybridization. The method of the invention can therefore identify the hybridization between test RNA and the nucleic acid probe, and further confirms the existence of the desired target sequence in the test nucleic acid.

On the other hand, the RNA sequence of *A. hydrophilia* could not base-pair with the nucleic acid probe. The voltage value measured is also higher before washing because the nucleic acid probe (labeled with fluorescent dye) was also filled in the pores of the substrate. The values dropped to 0.00000589 mV after the first and the second washing processes respectively, which is quite close to the background value of 0.00000591 mV. The feasibility of the method of the invention is further confirmed with no occurrence of pseudo-positive result.

What is claimed is:

1. A method of nucleic acid hybridization, comprising the steps of:
   (1) providing a test nucleic acid and a nucleic acid probe labeled with a detectable marker that is capable of generating a signal;
   (2) mixing the test nucleic acid and the nucleic acid probe for base pairing and obtaining a mixed solution;
   (3) providing a hybridization device having a hybridization region installed with a porous substrate that has a pore diameter ranging from 0.01-50 μm and is a positively charged nylon membrane, the hybridization region being connected to at least one first inlet/outlet hole and at least one second inlet/outlet hole, respectively, wherein the hybridization device is a microfluidic chip;
   (4) feeding the mixed solution obtained from step (2) into at least one of the at least one first inlet/outlet hole to flow the mixed solution through the porous substrate so that the test nucleic acid is absorbed onto the porous substrate, and flowing the mixed solution that has passed through the porous substrate out from at least one of the at least one second inlet/outlet hole;
   (5) providing a washing solution that is a salt solution effective to remove the nucleic acid probe that is unhybridized to the test nucleic acid from step (2) from the porous substrate, feeding the washing solution into at least one of the at least one first inlet/outlet hole to flow the washing solution through the porous substrate, and flowing the washing solution that has passed through the porous substrate out from at least one of the at least one second inlet/outlet hole to remove the nucleic acid probe that is unhybridized to the test nucleic acid from step (2); and
   (6) detecting the signal generated by the detectable marker of the nucleic acid probe that is hybridized to the test nucleic acid on the porous substrate after step (5).

2. The method as claimed in claim 1, wherein an interstice with a defined width is formed between a lateral side of the porous substrate and the hybridization region.

3. The method as claimed in claim 1, wherein the porous substrate in step (3) is in a dry state.

4. The method as claimed in claim 1, wherein the hybridization region in the hybridization device is chamber-like.

5. The method as claimed in claim 1, wherein the test nucleic acid is DNA (deoxyribonucleic acid).

6. The method as claimed in claim 1, wherein the test nucleic acid is RNA (ribonucleic acid).

7. The method as claimed in claim 1, wherein the hybridization device comprises an upper basal plate and a lower basal plate that are stacked together to form the hybridization region, the upper basal plate has at least one of the at least one first inlet/outlet hole and at least one of the at least one second inlet/outlet hole connects to a lateral side of the hybridization region.

8. The method as claimed in claim 7, wherein an interstice with a defined width is formed between the lateral side of the porous substrate and the hybridization region.

9. The method as claimed in claim 7, wherein the hybridization region in the hybridization device is chamber-like.

10. The method as claimed in claim 9, wherein an interstice with a defined width is formed between the lateral side of the porous substrate and the hybridization region.

* * * * *